US00PP26836P3

(12) United States Plant Patent
Kordes

(10) Patent No.: US PP26,836 P3
(45) Date of Patent: Jun. 21, 2016

(54) SHRUB ROSE PLANT NAMED 'KORGEOWIM'

(50) Latin Name: *Rosa hybrida*
Varietal Denomination: KORgeowim

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 115 days.

(21) Appl. No.: 14/120,936

(22) Filed: Jul. 11, 2014

(65) Prior Publication Data

US 2016/0014939 P1 Jan. 14, 2016

(51) Int. Cl.
*A01H 5/02* (2006.01)

(52) U.S. Cl.
USPC ..... Plt./107

(58) Field of Classification Search
USPC ..... Plt./107
See application file for complete search history.

(56) References Cited

PUBLICATIONS

PLUTO Plant Variety Database Dec. 16, 2015. p. 1.*
HelpMeFind 2015. p. 1.*

* cited by examiner

*Primary Examiner* — Annette Para

(57) ABSTRACT

A new and distinct variety of rose with long lasting, novel pale lavender-pink flowers, and attractive foliage with excellent disease resistance. It exhibits an upright to bushy habit with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORgeowim'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2003. The crossing was between an un-named seedling, the seed parent, and another un-named seedling, the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORgeowin'.

SUMMARY OF THE INVENTION

The new rose plant may be distinguished from its seed parent, an un-named seedling, by the following combination of characteristics:

1. 'KORgeowim' has strong fragrance, whereas the un-named seedling has moderate fragrance.
2. 'KORgeowim' has excellent disease resistance, whereas the un-named seedling has above-average disease resistance.

The new rose plant may be distinguished from its pollen parent, an un-named seedling, by the following combination of characteristics:

1. 'KORgeowim' has a very double petal count, whereas the un-named seedling has a semi-double petal count.
2. 'KORgeowim' has medium flowers, whereas the un-named seedling has small flowers.

The objective of the hybridization was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORgeowim' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORgeowim' was selected in May 2004 from the seedling beds to be asexually propagated for further evaluation. The first asexual propagation of 'KORgeowim' was done by budding in July 2004 at the inventor's nursery in Offenseth-Sparrieshoop, Germany.

These initial and other subsequent propagations conducted in controlled environments demonstrate that 'KORgeowim' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORgeowim'.

DETAILED BOTANICAL DESCRIPTION

The following is a description of 'KORgeowim', as observed growing in May 2014 in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORpenparo', a rose variety from the same inventor described and illustrated in U.S. Plant Pat. No. 21,471 issued on Nov. 16, 2010 are compared to 'KORgeowim' in Chart 1.

CHART 1

| Characteristic | 'KORgeowim' | 'KORpenparo' |
|---|---|---|
| Fragrance. | Strong. | Light to Moderate. |
| General Tonality on Open Flower. | Red-Purple Group 69A. | Yellow-White Group 158B. |
| Petal Count. | 85 to 95 petals. | 45 petals. |

Parents:

*Seed parent*.—An un-named seedling.

*Pollen parent*.—An un-named seedling.

Classification:

*Botanical classification*.—*Rosa hybrida* 'KORgeowin'.

*Commercial classification*.—Shrub rose.

FLOWER AND FLOWER BUD

Blooming habit: Recurrent.

Flower bud:

*Size*.—Upon opening, 50 to 55 mm in length from base of receptacle to distal end of bud and 40 to 45 mm diameter at its widest point.

*Bud form*.—Long. Pointed ovoid.

*Bud color*.—As sepals first unfold, bud color is Yellow-Green Group 150D with intonations of Greyed-Red Group 180C in the marginal zones. When ¼ open, the upper surface of petals is White Group 155C, and the lower surface is White Group 155C. Guard Petals are White Group 155A.

*Sepals*.—Color: Upper surface is Yellow-Green Group 145C. Lower surface is Yellow-Green Group 145A. Intonations of Greyed-Purple Group 184B. Size: Average 25 mm (l)×10 mm (w). Shape: Weak foliaceous appendages on three of the five sepals. Apex: Apiculate. Base: Flat at union with receptacle. Quantity: Five. Surface texture: Upper side: Pubescent. Lower surface: Rough. Margins: Ciliate. Stipitate glands: Present on lower surface.

Flower bloom:

*Fragrance*.—Strong.

*Duration*.—On the plant 3 to 4 days. Senesced petals drop away cleanly.

*Size*.—Medium for a shrub rose. When open, the average flower diameter is 65 to 75 mm and the average flower height is 45 mm.

*Form*.—Shape of flower when viewed from the side: Upon opening, upper part: Convex. Upon opening, lower part: Flat. Open flower, upper part: Flattened concave. Open flower, lower part: Concave.

Color:

*Upon opening, petals*.—Outermost petals: Outer Side: White Group 155C. Inner Side: White Group 155C. Innermost petals: Outer Side: White Group N155C. Inner Side: White Group N155C.

*Upon opening, basal petal spots*.—Basal petal spot, outermost petals: Outer Side: Yellow Group 2D. Inner Side: Yellow Group 2C. Basal petal spot, innermost petals: Outer Side: Yellow Group 2D. Inner Side: Yellow Group 3D.

*After opening, petals*.—Outermost petals: Outer Side: White Group 155B in the basal and middle zones, White Group N155B in the marginal zone. Inner Side: White Group 155B in the basal and middle zones, White Group N155B in the marginal zone. Innermost petals: Outer Side: White Group 155B in the basal zone, Red-Purple Group 69B in the middle zone, Red-Purple Group 69A in the marginal zone. Inner Side: White Group N 155D in the basal zone, White Group N155C in the middle zone, Red-Purple Group 69B in the marginal zone.

*After opening, basal petal spots*.—Basal petal spot, outermost petals: Outermost petals: Outer Side: Yellow Group 2D. Inner Side: Yellow Group 2D. Basal petal spot, innermost petals: Outer Side: Yellow Group 2B. Inner Side: Green-Yellow Group 1D.

General tonality: On open flower Red-Purple Group 69A. No change in the general tonality at the end of the 3rd day. Afterwards, general tonality is White Group N155D.

Petals:

*Petal count*.—Very Double.

*Average range*.—Approximately 85-95 petals under normal conditions.

*Petal reflex*.—Petals reflex somewhat.

*Petal margin*.—Entire.

*Petal shape*.—Outermost petals: Orbicular. Innermost petals: Elliptical. Apex: Obtuse on all petals. Base: Cuneate on inner petals, obtuse on outer petals.

*Petal size*.—Outermost petals: 40 to 45 mm (l)×40 to 45 mm (w). Innermost petals: 25 to 35 mm (l)×15 to 20 mm (w).

*Petal arrangement*.—Formal.

*Texture*.—Smooth.

Petaloids:

*Petaloid count*.—Average of 6 to 10 per flower.

*Petaloid size*.—10 to 12 mm (l)×7 to 10 mm (w).

*Petaloid color*.—Inner side: White Group N155D. Outer side: White Group N155D.

*Petaloid texture*.—Smooth.

*Margins*.—Undulated.

*Petaloid shape*.—Most commonly elliptical. Apex: Acute. Base: Cuneate.

Reproductive organs:

*Pistils*.—Average. Approximately 60 present. Stigmas: Location: Slightly superior in position to anthers. Color: Greyed-Yellow Group 162B. Styles: Length: About 10 mm long. Color: Red-Purple Group 58B.

*Stamens*.—Approximately 100 on average and regularly arranged. Anthers: Size: Average 2.5 mm (l)×1 mm (w). Pollen: Generally present. Color: Greyed-Orange Group N163D. Filaments: Color: Yellow Group 12B. Length: 5 to 7 mm.

*Receptacle*.—Surface: Smooth. Color: Yellow-Green Group 154A. Shape: Urn-shaped. Texture: Glabrous. Size: 7 to 9 mm (h)×10 to 12 mm (w).

*Pedicel*.—Surface: With fine hairs and stipitate glands. Length: 45 to 55 mm average length. Diameter: 3 to 4 mm average diameter. Color: Yellow-Green Group N144D with intonations of Greyed-Purple Group 185C. Strength: Moderately strong. Texture: Papillate. Borne: Multiple flower buds per stem, generally 1 to 6. Flowers held upright.

*Peduncle*.—Length: 7 to 13 mm average length. Diameter: 3 to 4 mm average diameter. Color: Yellow-Green Group 146C with intonations of Greyed-Purple Group 185C. Strength: Strong. Borne: Multiple flower buds per stem, generally 1 to 6.

THE PLANT

*Growth*.—Vigorous.

*Plant habit*.—Upright to bushy. When grown as a field plant, the average plant height is 90 cm and the average plant width is 50 cm.

*Stems*.—Stem color: Young wood: Yellow-Green Group 144B. Older wood: Yellow-Green Group 144A. Intonations: Greyed-Purple Group 184A. Stem surface texture: Young wood: Smooth. Older wood: Smooth.

*Prickles*.—Present. Incidence: Average of 7 per each 10 cm of stem. Size: Average length: 6 mm. Color: Immature prickles: Yellow-Green Group 145A. Mature prickles: Yellow-Green Group N144C. Shape: Deeply concave. Anthocyanin: Color Greyed-Purple 185B. Strongly present on most prickles at all stages of development.

*Leaves*.—Normally 5 leaflets on normal leaves in middle of the stem. Venation pattern: Pyramidal net pattern. Leaf size: 105 to 165 mm (l)×85 to 140 mm (w). Abundance: Average.

*Leaflets*.—Size: Average size of the terminal leaflet is 60 mm (l)×60 mm (w). Shape: Ovate. Base: Obtuse. Apex: Cuspidate. Margins: Serrated. Surface: Upper: Semi-glossy. Lower: Matte. Texture: Upper side of leaflet: Leathery. Under side of leaflet: Smooth. Color, mature foliage: Upper Leaflet Surface: Yellow-Green Group 147A. Lower Leaflet Surface: Yellow-Green Group 146B. Color, juvenile foliage: Upper Leaflet Surface: Yellow-Green Group 146B. Lower Leaflet Surface: Yellow-Green Group 146C. Anthocyanin intonation: Greyed-Purple Group 183B. Location: On immature foliage, primarily on underside and along margins. Arrangement: Odd pinnate. Venation: Reticulate.

*Stipules*.—Size: 20 to 35 mm (l)×7 mm (w). Stipule color: Yellow-Green Group 144A. Anthocyanin: Greyed-Red Group 182B, limited intonations on upper side of mid rib. Stipitate glands: Limited numbers present on margins. Margins: Ciliate. Texture: Glabrous. Shape: Apex: Apiculate. Base: Flat.

*Petiole*.—Length: Average 30 to 45 mm. Diameter: Average 1.5 to 2 mm. Petiole color: Yellow-Green Group 146B. Underneath: Yellow-Green Group 146C. Margins: Pubescent. Anthocyanin: Greyed-Purple Group 184C, on prickles and occasionally on midrib and margins. Prickles: A few small prickles underneath. Stipitate Glands: Limited on margins. Texture: Pubescent.

*Petiole rachis*.—Length: Average 15 to 20 mm. Diameter: Average 1.5 mm. Color: Yellow-Green Group 146C. Anthocyanin: Greyed-Purple Group 183C on prickles, stipitate glands, and occasionally on margins. Margins: Pubescent. Prickles: A few small prickles underneath. Stipitate glands: Limited numbers of stipitate glands on underside and margins.

Hips/seed formation: None observed.

Winter hardiness: To date, the variety has been grown successfully in Zone 6.

Disease resistance: Excellent resistance to Powdery mildew (*Sphaerotheca pannosa*) and blackspot (*Diplocarpon rosae*) diseases under normal growing conditions in Jackson County, Oreg.

I claim:

1. A new and distinct variety of rose plant, as described and illustrated herein.

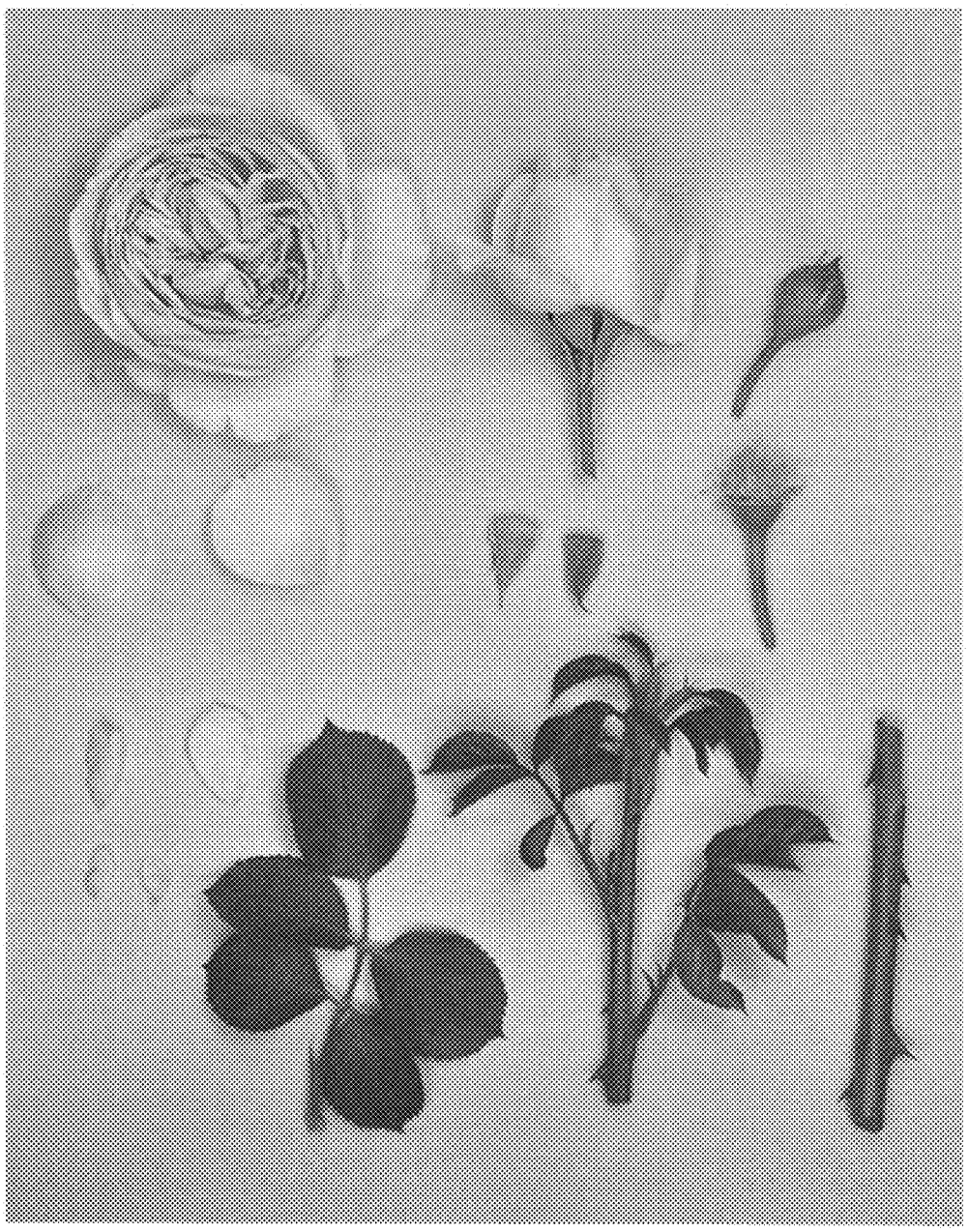

* * * * *